United States Patent [19]
Kiel et al.

[11] Patent Number: 5,663,443
[45] Date of Patent: Sep. 2, 1997

[54] RUTHENIUM CATALYSTS, THEIR PREPARATION AND A PROCESS FOR PREPARING CYCLOALIPHATIC POLYAMINES USING THESE CATALYSTS

[75] Inventors: Wolfgang Kiel, Odenthal; Eberhard Zirngiebl, Köln; Joerg-Dietrich Jentsch, Mülheim an der Ruhr, all of Germany

[73] Assignee: Bayer Aktiengesellschaft, Leverkusen, Germany

[21] Appl. No.: 384,303

[22] Filed: Feb. 3, 1995

[30]  Foreign Application Priority Data

Feb. 10, 1994 [DE] Germany ............................ 44 04 220.5

[51] Int. Cl.$^6$ .................................................. C07C 209/72
[52] U.S. Cl. ......................... 564/451; 502/304; 502/324; 564/452
[58] Field of Search ...................... 502/304, 324, 502/325; 564/451, 452

[56]  References Cited

U.S. PATENT DOCUMENTS

| | | | |
|---|---|---|---|
| 2,284,468 | 5/1942 | Burk et al. | 260/668 |
| 3,983,072 | 9/1976 | Stephens | 252/460 |
| 4,161,492 | 7/1979 | Weissel | 260/563 R |
| 4,186,145 | 1/1980 | Weissel | 260/563 D |
| 4,581,343 | 4/1986 | Blanchard et al. | 502/241 |
| 4,849,544 | 7/1989 | Culley et al. | 564/461 |
| 4,943,549 | 7/1990 | Immel et al. | 502/304 |
| 5,134,109 | 7/1992 | Uchiyama et al. | 502/324 |
| 5,245,082 | 9/1993 | Immel et al. | 564/451 |
| 5,386,060 | 1/1995 | Immel et al. | 564/450 |

FOREIGN PATENT DOCUMENTS

| | | |
|---|---|---|
| 0001425 | 4/1979 | European Pat. Off. . |
| 0351661 | 1/1990 | European Pat. Off. . |
| 0476359 | 3/1992 | European Pat. Off. . |
| 0503347 | 9/1992 | European Pat. Off. . |
| 2502893 | 7/1976 | Germany . |

*Primary Examiner*—Richard L. Raymond
*Attorney, Agent, or Firm*—Sprung Horn Kramer & Woods

[57]  ABSTRACT

Novel ruthenium catalysts additionally contain carbonates, hydroxides and/or hydrated oxides of cerium and manganese or of manganese and/or dehydration products thereof. They can optionally be present on a support material and can be prepared by converting soluble compounds of ruthenium, cerium and manganese by treatment with alkaline compounds into insoluble compounds and optionally further treating these. Such catalysts are particularly suitable for the preparation of cycloaliphatic polyamines by hydrogenation of corresponding aromatic amines.

8 Claims, No Drawings

RUTHENIUM CATALYSTS, THEIR PREPARATION AND A PROCESS FOR PREPARING CYCLOALIPHATIC POLYAMINES USING THESE CATALYSTS

The present invention relates to novel ruthenium catalysts, processes for their preparation and a process for preparing cycloaliphatic polyamines by catalytic hydrogenation of the corresponding aromatic amines using the novel ruthenium catalysts.

It is known that aromatic polyamines can be hydrogenated in the presence of ruthenium catalysts and the corresponding cycloaliphatic polyamines can thus be prepared. U.S. Pat. No. 4,849,544 describes supported ruthenium catalysts which additionally contain alkali metal hydroxides, alkali metal alkoxides or alkali metal amide salts of m-phenylenediamine and their use for preparing 1,3-diaminocyclohexanes from m-phenylenediamines. Disadvantages in this process are the long reaction time of from 17 to 24 hours and the sometimes low yields, with which the 1,3-diminocyclohexanes are obtained (see the examples of this U.S. patent Specification).

Good results are obtained if, in the preparation of cycloaliphatic polyamines from the corresponding aromatic amines, the catalysts used contain ruthenium and hydroxides and/or hydrated oxides of chromium and manganese and/or dehydration products thereof (see German Offenlegungsschrift 2 502 893). However, it is a disadvantage in this process that preparation of the catalyst gives precipitates which can be filtered only with great difficulty. In addition, it is necessary to dispose of chromium-containing waste water, which requires considerable effort and expense.

Cycloaliphatic polyamines are important starting materials for preparing polycondensation plastics and surface coatings, for example based on polyureas, polyamides and polyurethanes. They are also used as hardeners in epoxy resins. In the field of surface coatings, cycloaliphatic polyamines have achieved particular importance, since they are of a pale colour and give the surface coatings produced therefrom high yellowing resistance and high resistance to aggressive chemicals.

Ruthenium catalysts have now been found which are characterized in that they additionally contain carbonates, hydroxides and/or hydrated oxides of cerium and manganese or of manganese and/or dehydration products thereof.

The ruthenium content of catalysts of the invention can be, for example, from 0.1 to 20% by weight, calculated as elemental ruthenium. This content is preferably in the range from 0.5 to 5% by weight.

The weight ratio of cerium to manganese, likewise calculated as elements, can be, for example, from 0 to 5:1. Preferably this ratio is in the range from 0.1 to 3:1, particularly preferably in the range from 0.8 to 2:1.

Catalysts of the invention do not need to contain any other constituents apart from ruthenium in metallic or combined form and carbonates, hydroxides and/or hydrated oxides of cerium and manganese or of manganese and/or dehydration products thereof. However, during catalyst preparation, they can also contain customary additives and/or auxiliaries, for example water, tabletting aids, binders, agents for introducing porosity and/or fillers.

Catalysts of the invention can also be applied to a support material. Suitable support materials are, for example, aluminium oxide, silicon dioxide, kieselguhr, pumice, iron oxides, aluminium silicates, barium sulphate, carbon and niobic acid. Other known support materials for catalysts are also possible. The weight ratio of cerium and manganese to the support material can be, for example, from 0.1 to 2:1.

Catalysts of the invention can be prepared, for example, by converting soluble compounds of ruthenium, cerium and manganese or of ruthenium and manganese by treatment with alkaline compounds into insoluble compounds and optionally further treating these. For example, the essential catalyst components can be converted together into insoluble compounds. It is also possible to first convert only soluble cerium and manganese compounds or only manganese compounds into insoluble compounds, optionally treat these further, for example filtration and drying, and then to apply a soluble or insoluble ruthenium compound thereon and optionally further treat the product once again. As the last named further treatment, it is possible to carry out, for example, a treatment with reducing agents. Suitable reducing agents for this purpose are, for example, hydrazine hydrate, formic acid, formates and ascorbic acid.

Suitable soluble compounds of ruthenium, cerium and manganese are, in particular, ruthenium(III) nitrate, ruthenium(III) chloride, cerium(III) nitrate and manganese (II) nitrate, which can optionally contain water of hydration. The conversion into insoluble ruthenium compounds and carbonates, hydroxides or hydrated oxides of cerium and manganese or of manganese is carried out by additions of alkaline compounds. For example, these may be alkali metal carbonates and alkali metal hydroxides.

Optionally, a further treatment by filtration, washing free of soluble constituents, heat treatment, shaping and/or the complete or partial reduction of the ruthenium to the metal can be carried out.

The washing free of soluble constituents can, for example, be carried out until no more anions of the soluble compounds used can be detected in the washing water. The heat treatment can, for example, be drying at temperatures up to, for example, 120° C., optionally under reduced pressure. After such a drying, calcination can optionally be carried out at temperatures of, for example, from 200° to 450° C., preferably from 250° to 350° C.

After drying and optional calcination, catalysts of the invention can optionally be milled, homogenized and, for example together with customary auxiliaries, be formed into shaped bodies, for example pellets. It can be advantageous to reduce catalysts of the invention prior to their first use, for example by treatment with hydrogen at from 20° to 200° C. and pressures of from 0.1 to 350 bar.

For the preparation of pulverulent catalysts of the invention it can be advantageous to first prepare together the carbonates, hydroxides and/or hydrated oxides of cerium and manganese or of manganese and/or dehydration products thereof and then to carry out the precipitation of the ruthenium or of ruthenium compounds. In the preparation of agglomerated catalysts of the invention, the procedure can be, for example, to impregnate a jointly prepared dehydrated cerium and manganese hydroxide or manganese hydroxide only and/or corresponding hydrated oxides after shaping, for example palletizing, successively with a ruthenium salt solution and an alkali metal carbonate or hydroxide solution in any desired order, carry out intermediate drying after impregnation in each case and subsequently to wash with water. It is also possible to spray the ruthenium salt solution and alkali metal carbonate or hydroxide solution successively in a heated coating drum onto shaped and dehydrated cerium and manganese hydroxide or manganese hydroxide only and/or corresponding hydrated oxides and then to wash these. The number of impregnation or coating steps depends on the amount of ruthenium to be applied.

The present invention further provides a process for preparing cycloaliphatic polyamines by catalytic hydrogenation of corresponding aromatic amines in the presence of a ruthenium catalyst, which is characterized in that the catalyst used contains carbonates, hydroxides and/or hydrated oxides of cerium and manganese or of manganese and/or dehydration products thereof in addition to ruthenium in metallic or combined form.

Further details of the catalysts to be used and ways of preparing them are described further above.

In the process of the invention, the aromatic amines used can, for example, have the formula (I)

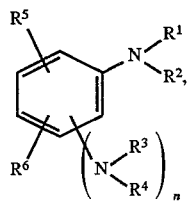

where
- $R^1$, $R^2$, $R^3$ and $R^4$ are identical or different and in each case represent hydrogen or $C_1$–$C_{10}$-alkyl,
- $R^5$ and $R^6$ are identical or different and in each case represent hydrogen, hydroxyl, $C_1$–$C_{10}$-alkyl, $C_5$–$C_{10}$-cycloalkyl or $C_6$–$C_{14}$-aryl, with these alkyl, cycloalkyl and aryl radicals optionally being able to be substituted by hydroxyl and/or $NH_2$ groups and
- n represents 1 or 2.

Preferred alkyl radicals are methyl, ethyl, propyl, isopropyl, butyl, isobutyl, tert-butyl, pentyl and hexyl.

Preferred cycloalkyls are cyclopentyl and cyclohexyl.
Preferred aryl radicals are phenyl and naphthyl.
Particularly preferred compounds of the formula (I) are:
- 2,4-, 2,6-, 2,3- and 2,5-diamino-methylbenzene and mixtures containing these compounds,
- 2,4-, 2,6-, 2,5- and 2,3-diamino-isopropylbenzene and mixtures containing these compounds,
- 2,4- and 2,6-diamino-3,5-diethyl-methylbenzene and mixtures containing these compounds,
- 2,4,6-triamino-methylbenzene, 2,4-diamino-isobutylbenzene and o-, m- and p-phenylenediamine and also 2,4-diamino-phenol.

In the process of the invention, the aromatic amines used can also, for example, have the formula (II)

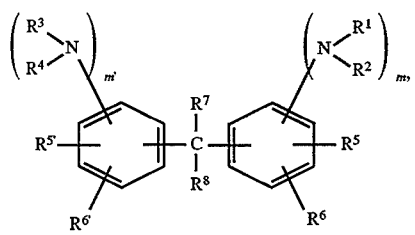

where
- $R^1$ to $R^6$ have the general and preferred meanings given for formula (I),
- $R^{5'}$ and $R^{6'}$ can, in terms of scope, have the general and preferred meanings given for formula (I) for $R^5$ and $R^6$, but can be different from $R^5$ and $R^6$,
- $R^7$ and $R^8$ are identical or different end in each case represent hydrogen or $C_1$–$C_{10}$-alkyl and
- m and m' are identical or different end in each case represent zero, 1 or 2, with m+m' being at least 2.

$R^7$ end $R^8$ are preferably identical end preferably represent methyl, ethyl or isopropyl.

Particularly preferred compounds of the formula (II) are 3,4,4'-triamino-3,3'-dimethyl-diphenylmethane, 2,4,4'-triamino-3,3'-diisopropyldiphenylmethane, 2,4,4'-triamino-3-isopropyldiphenylmethane, 2,4,4'-triamino-3-methyl-diphenylmethane and 2,2',4,4'-tetraamino-3,3'-dimethyldiphenylmethane.

In the process of the invention, the aromatic amines used can also, for example, have the formula (III)

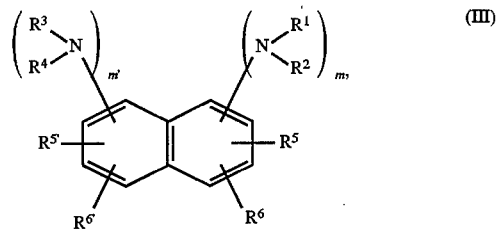

where
- $R^1$ to $R^6$ have the general and preferred meanings given for formula (I),
- $R^{5'}$ and $R^{6'}$ have the general and preferred meanings given for formula (II) and
- m and m' have the meanings given for formula (II), with m+m' being at least 2.

The process of the invention is generally carried out at elevated temperature and elevated pressure, for example at from 100° to 360° C. and from 50 to 400 bar, preferably from 180° to 300° C. and from 150 to 360 bar.

In general, the process of the invention can be carried out without addition of solvents. In particular, if aromatic amines melting above the intended reaction temperature are to be used, it is also possible to add solvents, for example cyclohexane, methylcyclohexane and/or tert-butanol.

The amount of catalyst can, for example, be calculated so that there are from 0.05 to 5 g of ruthenium (calculated as metal) present in the catalyst per kg of aromatic amine used. This amount is preferably from 0.1 to 2 g, in particular from 0.2 to 1 g.

The process of the invention can be carried out continuously or batchwise. For the batchwise procedure, suitable reactors are, for example, stirring autoclaves or loop reactors, into which the catalyst is introduced, preferably in pulverulent form, and the reaction is preferably carried out in the liquid phase.

The process of the invention is preferably carried out continuously, for example using pulverulent catalyst according to the bubble column principle, by passing liquid or dissolved aromatic amine in which the catalyst is suspended, together with hydrogen in cocurrent through a reaction cascade. It is also possible, for example, to use agglomerated catalyst by allowing liquid or dissolved aromatic amine to trickle over a catalyst fixed in a reaction tube, while hydrogen is passed through the reaction tube in cocurrent or countercurrent.

Particularly in the continuous method of operating, it is advantageous to use hydrogen in excess and to circulate unreacted hydrogen.

Other embodiments are also possible for the process of the invention.

Using the method of the invention, the aromatic amines used give the corresponding cycloaliphatic polyamines. For example, aromatic amines of the formula (I) give cycloaliphatic polyamines of the formula (Ia)

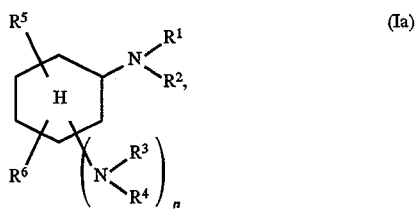

where the symbols used have the meanings given for formula (I).

Correspondingly, aromatic amines of the formula (II) give cycloaliphatic polyamines of the formula (IIa)

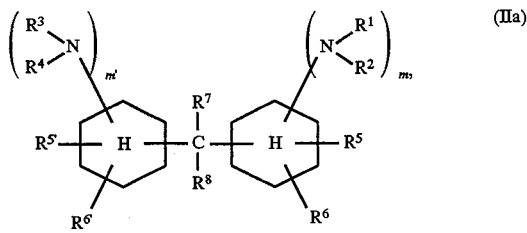

where the symbols used have the meanings given for the formula (II), and aromatic amines of the formula (III) give cycloaliphatic polyamines of the formula (IIIa)

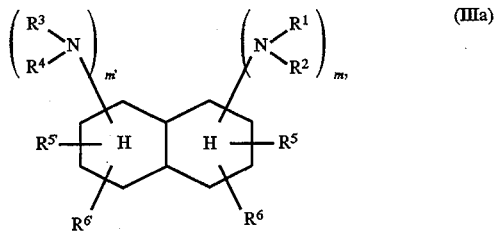

where the symbols used have the meanings given for the formula (III).

Optionally, the reaction mixture containing cycloaliphatic polyamine obtained after carrying out the process of the invention can be further purified, for example by distillation and/or crystallization.

The process of the invention has a series of surprising advantages: it allows the preparation of cycloaliphatic polyamines with high selectivities and with short reaction times or high throughput per amount of catalyst. The preparation of the catalyst is simple, since only readily filterable precipitates and no waste water requiring special disposal are formed. Finally, even after prolonged operating times, the catalyst does not lose its selectivity and the hydrogenation rate achievable with it does not fall. Frequently the catalyst activity even increases after prolonged operating times.

EXAMPLE 1

7 l of demineralized water was initially charged and 1074 g of $Ce(NO_3)_3.H_2O$, 1583 g of $Mn(NO_3)_2.4H_2O$ and 146 g of $Ru(NO_3)_3$ were added. The solids were dissolved with stirring and the solution was heated to 85° C. Subsequently, at this temperature, 1201 g of $Na_2CO_3$, dissolved in 5 l of demineralized water, were metered in and finally 115.5 g of hydrazine hydrate (23.6% strength by weight) dissolved in 4.5 l of demineralized water were metered in. The suspension formed was stirred for a further 1.5 hours. The mixture was then cooled and the precipitate was filtered off. The filter cake was washed free of nitrate using demineralized water, dried at from 100° to 110° C. and then milled. Subsequently, the powder formed was calcined for 4 hours at 300° C.

EXAMPLE 2

100 g of $\gamma$-$Al_2O_3$ in powdered form were suspended in 100 ml of water and 33.09 g of $Ce(NO_3)_3.6H_2O$, 26.32 g of $Mn(NO_3)_2.4H_2O$ and 6.25 g of Ru in the form of a $Ru(NO_3)_3$ solution were dissolved in water and in the form of 700 ml of liquid were added to the $Al_2O_3$ suspension. The mixture formed was heated to 85° C. and 26.25 g of sodium hydroxide, dissolved in 200 ml of water, was then added dropwise at 85° C. while stirring and the mixture was stirred for a further 1.5 hours at 85° C. The separation and further treatment of the precipitate was carried out in the same way as described in Example 1.

EXAMPLE 3

200 g of a mixture of 65% by weight of 2,4-diaminotoluene and 35% by weight of 2,6-diaminotoluene were hydrogenated in a 0.7 l autoclave at from 220° to 240° C. and at from 150 to 180 bar in the presence of 6.4 g of the catalyst obtained as described in Example 1 until hydrogen uptake ceased. The reaction was complete after 2.5 hours. The reaction mixture contained 94% by weight of 2,4- and 2,6-diaminomethylcyclohexane (mixture 65:35) and 5% by weight of methylcyclohexylamine.

The filtration time in the preparation of the catalyst was 45 seconds.

EXAMPLE 4

Example 3 was repeated a number of times, always using the catalyst which was already present in the previous charge. The hydrogenation time and the composition of the reaction mixture were as shown in the following table:

| Catalyst from Example No. | Example No. | Hydrogenation time [min] | Present in the reaction mixture [% by weight] | |
|---|---|---|---|---|
| | | | Diminomethyl-cyclohexane | Methylcyclo-hexylamine |
| 4a | 3 | 173 | 91.4 | 6.2 |
| 4b | 4a | 118 | 93.3 | 6.2 |
| 4c | 4b | 115 | 94.9 | 4.5 |

EXAMPLE 5

(Comparative Example)

The procedure was as in Example 3, but using a Ru/Mn/Cr catalyst prepared as described in Example 1 of German Offenlegungsschrift 2 502 893. The reaction was complete after 293 minutes, the hydrogenated mixture contained 93% by weight of diaminomethylcyclohexane and 6% by weight of methylcyclohexylamine.

The filtration time in the preparation of the catalyst was 5.5 minutes.

EXAMPLE 6

100 g of the toluylenediamine mixture also used in Example 3, 100 g of cyclohexane and 3.2 g of the catalyst obtained as described in Example 1 were hydrogenated with hydrogen in an autoclave at 220° C. and 180 bar. The hydrogenation was complete after 320 minutes. The reaction mixture then contained 92% by weight of diaminomethylcyclohexane.

EXAMPLE 7

200 g of 2,4-diaminocumene were hydrogenated in a 0.7 l autoclave at from 230° to 270° C. and from 150 to 180 bar using 6.4 g of catalyst obtained as described in Example 1 until hydrogen uptake had ceased. The reaction was complete after 60 minutes. The hydrogenated mixture then contained 90.7% by weight of 2,4-diaminoisopropylcyclohexane and 8.3% by weight of isopropylcyclohexylamine.

EXAMPLE 8

200 g of 2,4-diethyldiaminotoluene were hydrogenated in a 0.7 l autoclave at from 240° to 280° C. and from 150 to 180 bar using 6.4 g of the catalyst obtained as described in Example 1 until hydrogen uptake had ceased. The reaction was complete after 120 minutes. The hydrogenated mixture then present contained 95.3% by weight of 2,4-diethylmethyldiaminocyclohexane.

EXAMPLE 9

200 g of 2,4,6-triisopropyl-1,3-diaminobenzene were hydrogenated in a 0.7 l autoclave at from 240° to 280° C. and from 150 to 180 bar using 6.4 g of the catalyst obtained as described in Example 1 until hydrogen uptake had ceased. The reaction was complete after 180 minutes. The hydrogenated mixture then present contained 85.8% by weight of 2,4,6-triisopropyl-1,3-diaminocyclohexane and 8.8% by weight of triisopropylcyclohexylamine.

EXAMPLE 10

The procedure was as described in Example 3, but using a catalyst which had been prepared as described in Example 1, but omitting the cerium nitrate. The reaction was complete after 3 hours and the reaction mixture contained 90.6% by weight of diaminomethylcyclohexane and 5.6% by weight of methylcyclohexylamine.

What is claimed is:

1. A ruthenium catalyst which consists essentially of ruthenium and either i) a carbonate, hydroxide and/or hydrated oxide of cerium and maganese; or ii) maganese alone and/or a dehydration product thereof wherein the catalyst is in a pulverulent form and wherein the essential catalytic components are converted together into an insoluble compound by treatment with an alkaline compound and wherein said catalyst is optionally applied to a support.

2. The ruthenium catalyst of claim 1, in which the ruthenium content is from 0.1 to 20% by weight (calculated as elemental ruthenium), based on the total weight of the catalyst, the weight ratio of cerium to manganese (calculated as elements) is from 0 to 5:1 and the weight ratio of cerium and manganese to the support material is from 0.1 to 2:1.

3. The catalyst according to claim 1, in which after the essential catalytic components are converted together to an insoluble compound, it is further treated by filtering, washing free the soluble components, heating, and shaping and/or reducing the ruthenium.

4. The catalyst according to claim 2, wherein during heating, the material is dried at a temperature of up to 120° C. and then calcined at a temperature of from 200° to 450° C.

5. A process for preparing a cycloaliphatic polyamine which comprises catalytically hydrogenating an aromatic amine of the formula

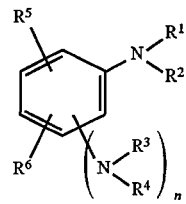

where $R^1$, $R^2$, $R^3$ and $R^4$ are identical or different and in each case represent hydrogen or $C_1$–$C_{10}$-alkyl, $R^5$ and $R^6$ are identical or different and in each case represent hydrogen, hydroxyl, $C_1$–$C_{10}$-alkyl, $C_5$–$C_{10}$-cycloalkyl or $C_6$–$C_{14}$-aryl, wherein said alkyl, cycloalkyl, and aryl moieties are optionally substituted by a hydroxyl and/or an $NH_2$ group, and n represents 1 or 2;

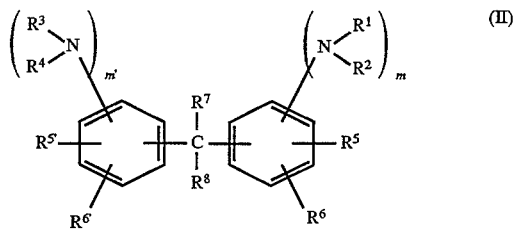

where $R^1$ to $R^6$ are as defined above, $R^{5'}$ and $R^{6'}$ are identical or different and in each case represent hydrogen, hydroxyl, $C_1$–$C_{10}$-alkyl, $C_5$–$C_{10}$-cycloalkyl or $C_6$–$C_{14}$-aryl, wherein said alkyl, cycloalkyl, and aryl moieties are optionally substituted by a hydroxyl and/or an $NH_2$ group, m and m' are 2; or

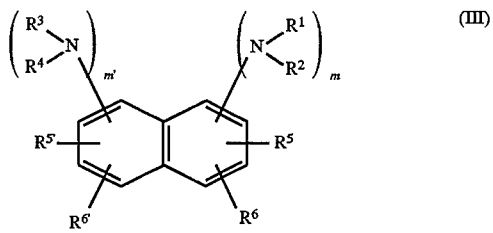

where $R^1$ to $R^6$ are as defined above, $R^{5'}$ and $R^{6'}$ are defined above, and m and m' are 2, in the presence of a ruthenium catalyst according to claim 1 and in the liquid phase.

6. The process according to claim 5, wherein the ruthenium content is from 0.1 to 20% by weight (calculated as elemental ruthenium), based on the total weight of the catalyst, the weight ratio of cerium to manganese (calculated as elements) is from 0 to 5:1 and the weight ratio or cerium and manganese to the support material is from 0.1 to 2:1.

7. The process of claim 5, which is carried out at from 100° to 360° C. and from 50 to 400 bar.

8. The process of claim 5, in which from 0.05 to 5 g of ruthenium (calculated as metal) are used per kg of aromatic amine.

* * * * *